(12) United States Patent
Ogedengbe

(10) Patent No.: US 11,490,748 B1
(45) Date of Patent: Nov. 8, 2022

(54) EFFORTLESS DUVET COVER

(71) Applicant: Lola Ogedengbe, Los Angeles, CA (US)

(72) Inventor: Lola Ogedengbe, Los Angeles, CA (US)

(73) Assignee: Lola Ogedengbe, Los Angeles, CA (US)

( * ) Notice: Subject to any disclaimer, the term of this patent is extended or adjusted under 35 U.S.C. 154(b) by 254 days.

(21) Appl. No.: 16/883,773

(22) Filed: May 26, 2020

Related U.S. Application Data (60) Provisional application No. 62/824,283, filed on Mar. 26, 2019.

(51) Int. Cl.
*A47G 9/02* (2006.01)
*A47G 9/04* (2006.01)
*A61M 21/00* (2006.01)

(52) U.S. Cl.
CPC ......... *A47G 9/0261* (2013.01); *A47G 9/0207* (2013.01); *A47G 9/0223* (2013.01); *A47G 9/04* (2013.01); *A61M 21/00* (2013.01); *A61M 2021/0022* (2013.01)

(58) Field of Classification Search
CPC .. A47G 9/0207; A47G 9/0223; A47G 9/0261; A47G 9/04; A61M 21/00; A61M 2021/0022
See application file for complete search history.

(56) References Cited

U.S. PATENT DOCUMENTS

| | | | |
|---|---|---|---|
| 1,817,404 | A | 8/1931 | Whaley |
| 2,060,092 | A | 9/1935 | Lucas |
| D216,610 | S | 2/1970 | Stiver |
| D230,117 | S | 1/1974 | Johnson |

(Continued)

FOREIGN PATENT DOCUMENTS

| | | |
|---|---|---|
| GB | 3021338 | 7/2005 |
| WO | D219737-001 | 4/2022 |

(Continued)

OTHER PUBLICATIONS

Beddley, The Revolutionary Easy-Open Duvet Cover, 3-Sided Zipper Opening, https://beddley.com: 2020. 7 pages.

(Continued)

*Primary Examiner* — David R Hare
*Assistant Examiner* — George Sun
(74) *Attorney, Agent, or Firm* — Stanek Lemon Crouse & Meeks, PA (57) ABSTRACT

A duvet cover for housing an assembly includes a top fabric panel and a bottom fabric panel that together form a flexible fabric envelope for receiving the duvet, wherein head edges of the top fabric panel and the bottom fabric panel are joined together and may form a permanently closed head edge. Side edges of the top fabric panel and the bottom fabric panel and foot edges of the top fabric panel and the bottom fabric panel edges may be equipped with closable fastening devices to engage each other thereby defining at least three closable edges and a composite fabric panel that forms a second end pocket at a foot edge of the bottom fabric panel. The foot edge of the composite fabric panel is joined with the foot edge of the bottom fabric panel securing the duvet in place inside the duvet cover.

20 Claims, 6 Drawing Sheets

(56) References Cited

U.S. PATENT DOCUMENTS

| | | | |
|---|---|---|---|
| 4,097,944 A | | 7/1978 | Yulish |
| D258,035 S | | 1/1981 | Fenwick |
| D274,493 S | | 7/1984 | Dyby |
| 4,654,906 A | | 4/1987 | Roberts |
| D397,269 S | | 8/1998 | Kawamoto |
| D522,299 S | | 6/2006 | Robbins, III |
| D530,059 S | | 10/2006 | Tenenbaum |
| D589,735 S | | 4/2009 | Kaiser |
| D647,225 S | | 10/2011 | Boyer |
| D657,987 S | | 4/2012 | Lane |
| 8,458,832 B1 | * | 6/2013 | Krishna ............... A47G 9/0261 5/501 |
| D702,072 S | | 4/2014 | Neff |
| D745,791 S | | 12/2015 | Corley |
| D861,376 S | | 10/2019 | Malouf |
| D867,019 S | | 11/2019 | Jenkins |
| D879,503 S | | 3/2020 | Fu |
| D887,177 S | | 6/2020 | Amoyal |
| 10,881,225 B1 | * | 1/2021 | Bernick ............... A47G 9/0207 |
| D919,332 S | | 5/2021 | Witbeck |
| D931,653 S | | 9/2021 | Sun |
| D932,213 S | | 10/2021 | Bang |
| D935,187 S | | 11/2021 | Hu |
| 2002/0095725 A1 | | 7/2002 | Dix |
| 2005/0144721 A1 | * | 7/2005 | Linnane ............... A47G 9/0261 5/501 |
| 2011/0023235 A1 | * | 2/2011 | Gold ............... A47G 9/0261 112/475.16 |
| 2014/0013507 A1 | * | 1/2014 | Perez ............... A47G 9/02 101/483 |
| 2017/0086606 A1 | * | 3/2017 | Kassab Arabo ......... A45C 3/00 |
| 2018/0168372 A1 | * | 6/2018 | Pool ............... A47G 9/0207 |
| 2019/0099019 A1 | * | 4/2019 | Heiman ............... A47G 9/0261 |
| 2019/0223630 A1 | * | 7/2019 | Phan ............... A47G 9/0261 |
| 2020/0060447 A1 | * | 2/2020 | Fravel ............... A47G 9/0261 |

FOREIGN PATENT DOCUMENTS

| | | |
|---|---|---|
| WO | D219737-002 | 4/2022 |
| WO | D219737-003 | 4/2022 |
| WO | D219737-004 | 4/2022 |

OTHER PUBLICATIONS

Google Image Search: "Duvet Cover," [online], [site visited May 2, 2022], Available from Internet, <URL: {Year: 2022).
[Cite U count:] https://www.google.com/search?q=duvet+cover&sxsrf=ALiCzsZ0cO4aYATvvYux-amX2DkLgiJFsQ:16515512216187&source=lnms&tbm=isch&sa=X&ved=2aHUKEwjdwsbcu8L3AhXehXIEHTdiC38Q_AuoAnoECAEQBA&biw=1200&bih=17778dpr=1> (Year: 2022).
Design Patent Search Report (Design 1)—Duvet Cover with Invisible Zipper/Exposed Zipper, dated Apr. 28, 2021, 24 pages.
Design Patent Search Report (Design 2)—Duvet Cover with Two Flanges that Conceal Zipper, dated Apr. 29, 2021, 22 pages.
Design Patent Search Report (Design 4)—Duvet Cover with Three-Sided Exposed Zipper, dated Apr. 28, 2021, 20 pages.
Design Patent Search Report (Design 5)—Three-Sided Zipper Duvet Cover with Foot-End Pocket, dated Apr. 20, 2021, 19 pages.

* cited by examiner

EFFORTLESS DUVET COVER

CROSS REFERENCE TO RELATED APPLICATION

This application claims priority to U.S. Provisional Patent Application No. 62/824,283, filed Mar. 26, 2019, the content of which is hereby incorporated herein in its entirety.

FIELD

The embodiments herein relate generally to bedclothes, e.g., beddings, and more particularly, a duvet cover that effortlessly facilitates the insertion of a duvet into the duvet cover and prevents the duvet from slipping around inside the duvet cover.

BACKGROUND

A duvet is a type of bedding that includes a flat flexible bag filled with feathers, down, wool, silk, synthetic fibers or the like and is protected by a removable cover, known as a duvet cover. The duvet cover is used to protect a duvet, for example, from soiling. A duvet may sometimes be referred to as a Comforter, Eiderdown, Deckbettbezug, "Housse pour coquette" or Quilt in some countries. A typical duvet cover comprises two panels of fabric fastened together, usually by stitching along the head end and their two parallel sides lengthwise, while the foot end is left free and unstitched. Thus, creating a large hard-to-maneuver envelope enclosure wherein inserting and removing the duvet from a duvet cover can be an arduous task.

Although, the duvet cover has been in use for decades, it has not been subject to much evolution to facilitate its use. For the elderly, the disabled, the physically fit and for everyone alike, it is an unpleasant and cumbersome task that most often requires two people to complete. Due to the sealed, restrictive design and limited access to the inside, it generally takes an inordinate length of time to insert and shove a duvet into a duvet cover and also to remove it for laundering or dry-cleaning. This not only impacts productivity, wastes precious time and creates undue stress, but it may also create hygiene issues if the owner finds it too troublesome to handle.

Accordingly, there remains a need for a duvet cover that makes it easier and faster for anyone to complete the insertion into or removal of a duvet from its duvet cover without the need to stuff, shove, struggle or feel frustrated.

SUMMARY

In view of the foregoing, an embodiment herein provides a cover for housing an assembly, including (i) a top fabric panel and a bottom fabric panel that together form a flexible fabric envelope for receiving the assembly. A head edge of said top fabric panel and said bottom fabric panel are joined together to form a closed head edge; side edges of said top fabric panel and said bottom fabric panel, next to said closed head edge, are partially joined together to form a first end pocket which spans the width of said top fabric panel and said bottom fabric panel; and remaining side edges of said top fabric panel and said bottom fabric panel and foot edges of said top fabric panel and said bottom fabric panel edges are equipped with a closable fastening device to engage each other thereby defining at least three edges that are closable and releasable and (ii) a composite fabric panel that forms a second end pocket at a foot edge of the bottom fabric panel, wherein said composite fabric panel is created by joining the foot edge of a third fabric panel with said foot edge of the bottom fabric panel; and side edges of said third fabric panel with side edges of the bottom fabric panel, next to said foot edge of the bottom fabric panel, wherein said first end pocket and said second end pocket serve as an insertion point for the assembly to be inserted into the head edge of the cover and the foot edge of the cover respectively, thereby securing the assembly in place inside the cover.

In some embodiments, said cover includes a clipping or binding accessory at four interior corners of the cover to keep the assembly in place and prevent the assembly from slipping away from the cover.

In some embodiments, said assembly is selected from a group including a duvet, a comforter, a bed-in-a-bag, a blanket, a quilt, and a multi layered material.

In some embodiments, a duvet cover for housing a duvet includes a top fabric panel and a bottom fabric panel that together form a flexible fabric envelope for receiving the duvet. A head edge of said top fabric panel and said bottom fabric panel are joined together to form a closed head edge; side edges of said top fabric panel and said bottom fabric panel, next to said closed head edge, are partially joined together to form a first end pocket which spans width of said top fabric panel and said bottom fabric panel; and remaining side edges of said top fabric panel and said bottom fabric panel and foot edges of said top fabric panel and said bottom fabric panel edges are equipped with a closable fastening device to engage each other thereby defining three closable edges, (ii) a composite fabric panel that forms a second end pocket at a foot edge of the bottom fabric panel, wherein said composite fabric panel is created by joining foot edge of a third fabric panel with said foot edge of the bottom fabric panel; and side edges of said third fabric panel with side edges of the bottom fabric panel, next to said foot edge of the bottom fabric panel, wherein said first end pocket and said second end pocket serve as an insertion point for the duvet to be inserted into the head edge of the duvet cover and the foot edge of the duvet cover respectively, thereby securing the duvet in place inside the duvet cover.

In some embodiments, an end pocket may be attached to a top panel, bottom panel or both.

In some embodiments, the duvet cover includes a clipping or binding accessory at four interior corners of the duvet cover to keep the duvet in place and prevent the duvet from being misaligned within the duvet cover.

In some embodiments, said clipping accessory includes at least one of buttons, clips, hooks and eyes, press studs, snaps, loops, ties, Velcro, etc. In some embodiments the clipping accessory is at least one of ties or clips.

In some embodiments, said closable fastening device is selected from a group including zippers, buttons, clips, hooks and eyes, press studs, snaps, loops, ties, Velcro.

In some embodiments, said closable fastening device includes two separate zipper chains and two separate zipper heads. A first end of each zipper chain begins at either side edge of the duvet cover and a second end of each zipper chain terminates at a midpoint of a foot edge of the duvet cover. The two separate zipper heads meet at the midpoint of the foot edge of the duvet cover when zipping the duvet cover.

In some embodiments, said closable fastening device includes a continuous zipper chain and two separate zipper heads. The two separate zipper heads meet at any point along the three closable edges when zipping the duvet cover. Optionally, one zipper head may be used in some embodiments.

In some embodiments, said second end pocket shields the duvet from being caught in the closable fastening device, thus facilitating engagement of the closable fastening device and preserving the integrity of the duvet itself.

In some embodiments, said duvet cover, and particularly the corners of the duvet cover, includes a shape of at least one of rounded, rectangular, square, hexagonal, rhombus or irregular.

In some embodiments, a coded corner system is used in the duvet cover to identify matching corners for laying the duvet cover correctly.

In some embodiments, a color-coded corner system is used to identify matching corners for laying the duvet cover correctly.

In some embodiments, one or more ties are attached to the four corners of the top fabric panel and bottom fabric panel to secure the duvet with optional ties attached along a head edge and/or foot edge of the duvet cover.

In some embodiments, the closable fastening device is a complementary closable fastening device.

These and other aspects of the embodiments herein will be better appreciated and understood when considered in conjunction with the following description and the accompanying drawings. It should be understood, however, that the following descriptions, while indicating embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiment will be better understood from the following detailed description with reference to the drawings, in which.

DETAILED DESCRIPTION

The embodiments described herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Notably, the embodiments presented herein provide a duvet cover that facilitates insertion into or removal of a duvet from its duvet cover and may also secure the positioning of the duvet. A closable fastening device is used to open and/or close the duvet cover and may also secure the duvet in position within the duvet cover. In addition to ease of operation and improved hygiene care, a fitted, custom look of a duvet cover and corresponding duvet can be achieved and maintained according to embodiments of the present inventive concept. Referring now to the drawings, and more particularly to FIG. 1 through FIG. 5, where similar reference characters denote corresponding features consistently throughout the figures, there are shown various embodiments.

Figure 1:
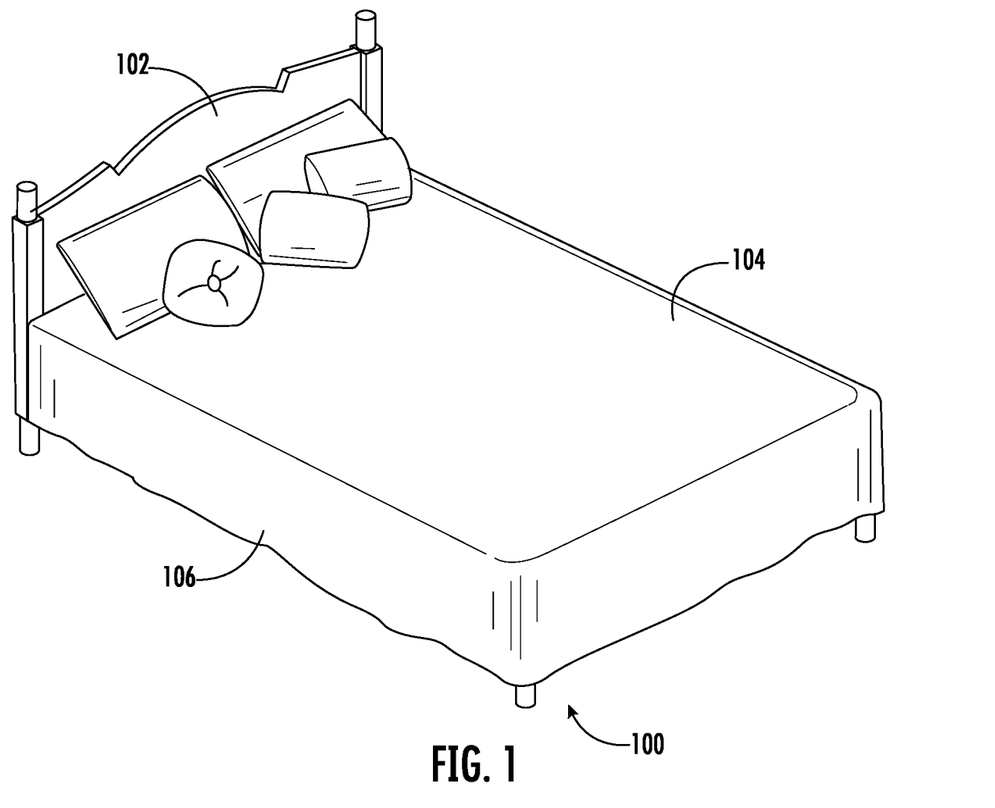
FIG. 1 illustrates a perspective view of a duvet cover used on a bed to cover a duvet according to some embodiments described herein.

FIG. 1 illustrates a perspective view of a duvet cover used on a bed to cover a duvet according to some embodiments described herein. The perspective view 100 includes a bed 102, a duvet 104, and a duvet cover 106. The bed 102 houses the duvet 104 and the duvet cover 106. The duvet cover 106 is associated with the duvet 104 to secure the duvet 104. In some embodiments, the duvet cover 106 includes a duvet 104. The duvet 104 refers to a type bedding that includes a structure filled with feathers, down, wool, silk, cotton, modal, synthetic fibers, recycled materials or the like and is protected by the duvet cover. As such, "duvet" encompasses terms such as comforter, blanket, quilt, etc. and combinations thereof when these bedding options are inserted into a duvet cover. The size of the duvet cover includes at least one of, but not limited to, a California king-sized bed, super king-sized bed, standard king-sized bed, queen-sized bed, full-sized bed, double-sized bed, three-quarter sized bed, twin-sized bed, XL twin-sized bed, single bed, toddler-sized bed, crib, cradle, bassinet, etc. Duvet sizes may also include any of the foregoing sizes being connected to a duvet cover of the same size or a different size to form a duvet cover of a desired size. For example, two twin sized duvet covers may be joined to form a king-sized duvet cover. The duvet covers may be permanently joined using known sewing/stitching or adhesive techniques or releasably joined using zippers, buttons, clips, hooks and eyes, press studs, snaps, loops, ties, Velcro and the like. Joining the duvet covers allows flexibility in the choice of using multiple duvets for one bedding assembly. In some embodiments, the design of the duvet 104 includes at least one of rounded, rectangular, square, hexagonal, rhombus or irregular shape. In some embodiments, two, three or four corners of the duvet 104 may be rounded, rectangular, square, hexagonal, rhombus or irregularly shaped. In some embodiments, two, three or four corners of the duvet cover 106 may be rounded, rectangular, square, hexagonal, rhombus or irregularly shaped. In some embodiments, two of the duvet cover corners may be one of a rounded, rectangular, square, hexagonal, rhombus or irregular shape and one or two of the remaining duvet cover corners is one of a rounded, rectangular, square, hexagonal, rhombus or irregular shape so long as the shape of two of the duvet cover corners is different from the shape of one or two of the other duvet cover corners. In some embodiments, one, two, three or four of the duvet cover corners are the same shape.

In some embodiments, the duvet cover 106 may cover one or more woven or non-woven materials. In some embodiments, the woven or the non-woven materials include at least one of quilt or a fleece, microfiber, wool sheet, modal, insulative material or recycled material and may be in the form of a comforter, blanket (including a weighted blanket), quilt, etc. The duvet cover 106 includes a closable fastening device for opening and closing the duvet cover 106 to secure the duvet 104 and/or prevent damage and/or soiling. In some embodiments, the duvet cover 106 includes a zipper chain and optionally a zipper head for closing and/or opening duvet cover 106. In some embodiments, the duvet cover 106 includes at least one of zippers, buttons, clips, hooks and eyes, press studs, snaps, loops, ties 220, Velcro for closing and opening duvet cover 106. In particular embodiments, the fastening device such as zippers, buttons, clips, hooks and eyes, press studs, snaps, loops, ties, Velcro, etc. is the same color as, similar to, or complementary to the color of the duvet cover 106. In some embodiments, the fastening device is nearly indistinguishable from the duvet cover 106 because of color and/or material. In some embodiments, the fastening device provides a stark contrast to the duvet cover 106 because of color and/or material and is very noticeable and distinguishable. In still other embodiments, the zippers, buttons, clips, hooks and eyes, press studs, snaps, loops, ties, Velcro, etc. conform to the shape of the corners of the duvet cover 106. In particular embodiments, a closable fastening device may be a zipper that is curved to accommodate a rounded shape of any foot edge and/or corner of the duvet cover 106. The curved zipper may provide unfettered and reliable operation of the zipper, while preserving the zipper's integrity.

Figure 2:
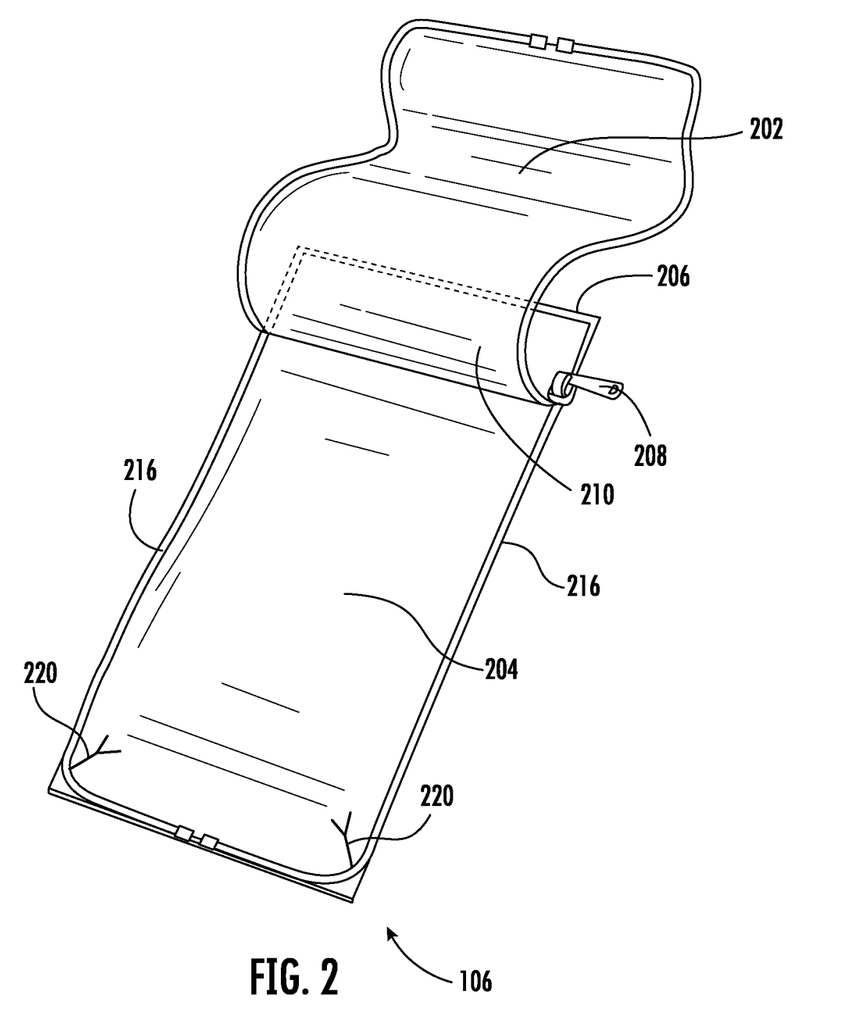
FIG. 2 illustrates a perspective view of a duvet cover in an open position of FIG. 1 according to some embodiments herein.

FIG. 2 illustrates a perspective view of a duvet cover 106 in an open position of FIG. 1 according to some embodiments herein. The duvet cover 106 includes a top fabric panel 202, a bottom fabric panel 204, head edge 206, closable fastening devices 208. The duvet cover 106 includes top fabric panel 202 and bottom fabric panel 204 to form a fabric envelope or folded-type structure. The first end of top fabric panel 202 and the first end of bottom fabric panel 204 are joined together to form the head edge 206. In some embodiments, the head edge 206 is closed to create an end pocket 210 to secure the duvet 104. In some embodiments, the side edges 216 of the top fabric panel 202 and bottom fabric panel 204 are partially joined at the first end on both sides to form a first end pocket 210. In some example embodiments, the length of the partially joined section of the top fabric panel 202 and bottom fabric panel 204 on either side is about 20 inches, creating the first end pocket 210 in the head edge 206. In some embodiments, the remaining side edges 216 of the top fabric panel 202 and bottom fabric panel 204 are not joined. In some embodiments, the width of the first end pocket 210 is created to receive the head side of the duvet 104. The closable fastening device 208 is attached with the one or more side edges of the top fabric panel 202, one or more side edges of the bottom fabric panel 204, a foot edge of the top fabric panel 202, a foot edge of the bottom fabric panel 204, for engaging and releasing the fastening device. In some embodiments, the closable fastening device is a complementary closable fastening device. The complementary closable fastening device may include a plurality of parts that work together to perform a plurality of actions. In some embodiments, the closable fastening device 208 includes at least one of zippers, buttons, clips, hooks and eyes, press studs, snaps, loops, ties 220, Velcro or other fasteners. In some embodiments, the zipper includes a zipper head, zipper pull, zipper slider, one or more zipper chains. In some embodiments the zipper head is connected at the top of the zipper chain to facilitate the opening and/or closing of the zipper. In some embodiments, when the zipper slider moves up, the zipper slider separates the one or more zipper chains. In some embodiments, when the zipper slider moves down, the zipper slider joins the one or more zipper chain. In some embodiments, the zipper includes at least one of plastic or metal. In some embodiments, the fasteners are placed in the side edges and bottom edges of the top fabric panel and bottom fabric panel with a predetermined distance. In some embodiments, at least one of the ties 220, or clips are placed in the top fabric panel 202 and the bottom fabric panel 204 with a predetermined distance to secure the duvet 104. In some embodiments, the two side edges and bottom edges of the top fabric panel 202 and the bottom fabric panel 204 present a releasable and/or closable opening. In some embodiments, the releasable and/or closable openings are used to lay the duvet 104 flat onto the duvet cover 106. The second end pocket 424 is created in the second end of the top fabric panel 202 and/or the second end of the bottom fabric panel 204 to secure the duvet 104. In some embodiments, the second end of the top fabric panel 202 and the second end of the bottom fabric panel 204 are attached to create a foot edge. In some embodiments, a head edge and a foot edge of the duvet 104 are inserted inside the duvet cover 106. In some embodiments, the top fabric panel 202 and the bottom fabric panel 204 include a dual zipper for durability. In some embodiments, the first zipper is placed in the right side of the top fabric panel and the bottom fabric panel. In some embodiments, the second zipper is placed in the opposite side of the top fabric panel and the bottom fabric panel. In some embodiments, the top fabric panel 202 and the bottom fabric panel 204 of duvet cover 106 are made of at least one of a suitable textile as described above. In some embodiments, the top fabric panel 202 and the bottom fabric panel 204 are made of at least one of woven, non-woven, modal, cotton, silk, lace, polyester or a cotton blend fabric. A composite fabric panel forms a second end pocket at a second end of the bottom fabric panel and/or the top fabric panel wherein, the composite fabric panel is created by joining the foot edge of a third fabric panel with said foot edge of the bottom fabric panel 204 and/or the top fabric panel 202 and side edges of the third fabric panel with side edges of the bottom fabric panel 204 and/or the top fabric panel 202, next to said foot edge of the bottom fabric panel and/or the top fabric panel. The first end pocket and the second end pocket serve as an insertion point for the duvet to be inserted into the head edge of the duvet cover and the foot edge of the duvet cover respectively for securing the duvet in place inside the cover. In some embodiments, the duvet cover 106 includes a clipping or binding accessory at two, three or four interior corners and optionally along the top edge of the duvet cover to keep the duvet 104 in place and prevent the duvet from slipping away from the duvet cover.

Figure 3A:
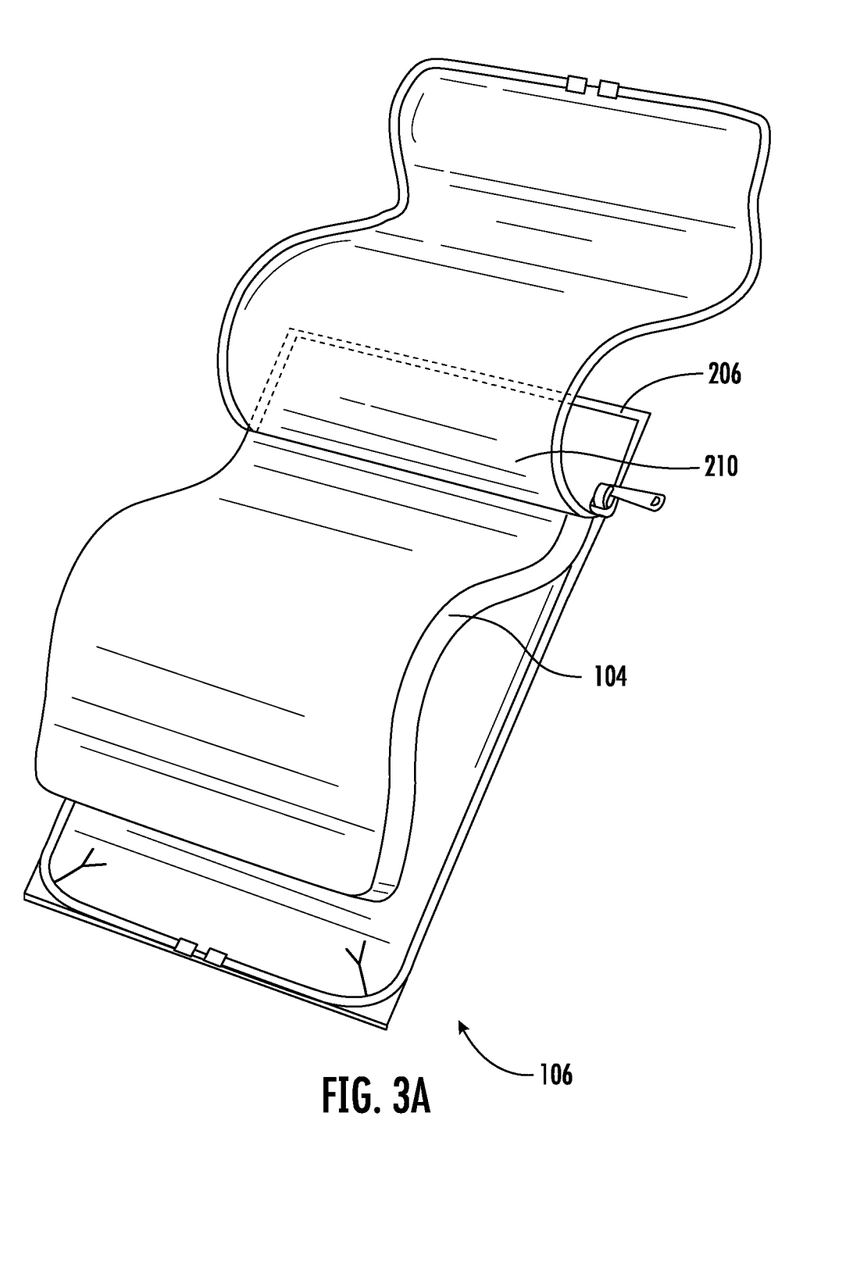
FIG. 3A illustrates a perspective view of inserting a duvet into a duvet cover of FIG. 2 according to some embodiments herein.

FIG. 3A illustrates a perspective view of inserting a duvet 104 into a duvet cover 106 of FIG. 2 according to some embodiments described herein. The duvet 104 is placed inside the duvet cover 106. The head edge 206 of the duvet cover 106 receives the head edge of the duvet 104 inside to secure the duvet 104 and/or prevent damage and/or soiling. Accordingly, the duvet cover 106 protects the duvet 104 placed inside. In some embodiments, the duvet cover provides an envelope look.

Figure 3B:
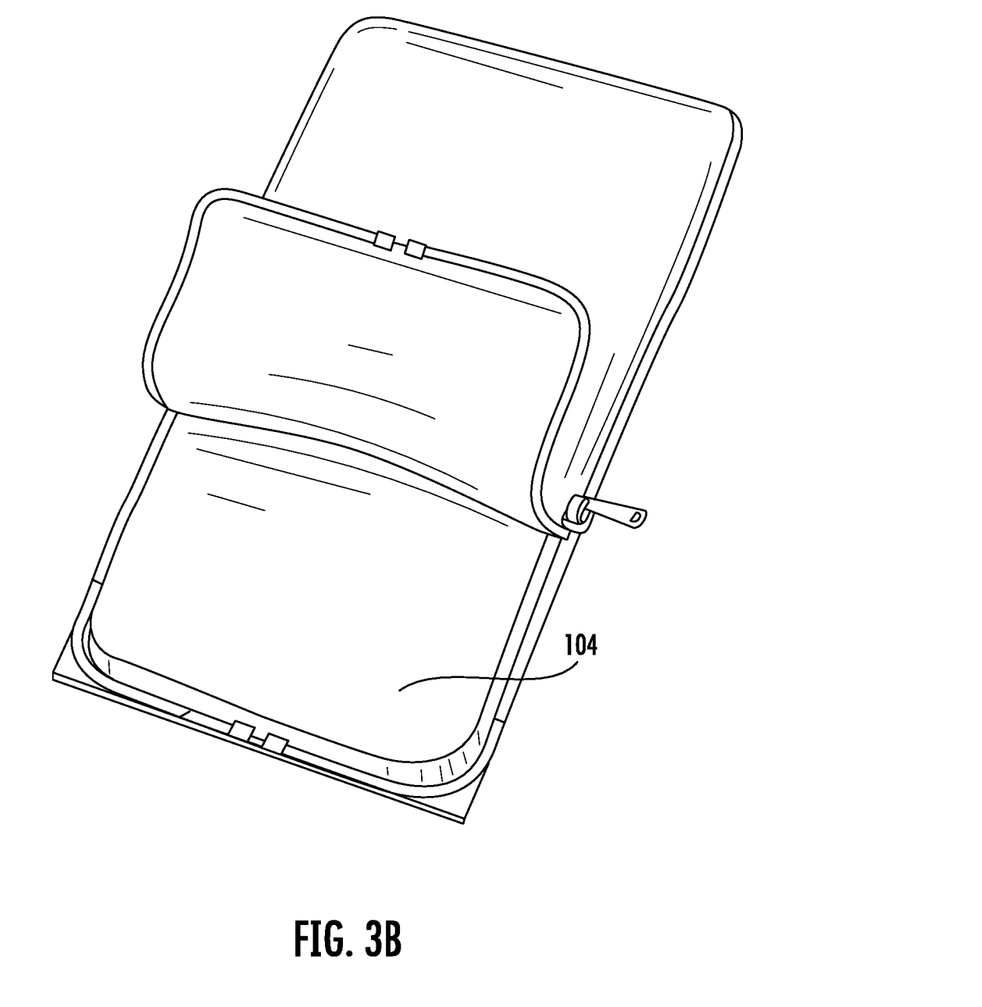
FIG. 3B illustrates a perspective view inside a duvet cover in a partially closed position of FIG. 2 according to some embodiments herein.

FIG. 3B illustrates a perspective view of duvet 104 inside a duvet cover 106 in a partially closed position of FIG. 1 according to some embodiments herein. The duvet 104 is partially covered by the duvet cover 106 to protect it from slipping and/or from possible damage and/or soiling. The duvet 104 is covered using the closable fastening device

208. In some embodiments, the duvet 104 is covered using complementary closable fastening device.

Figure 4:
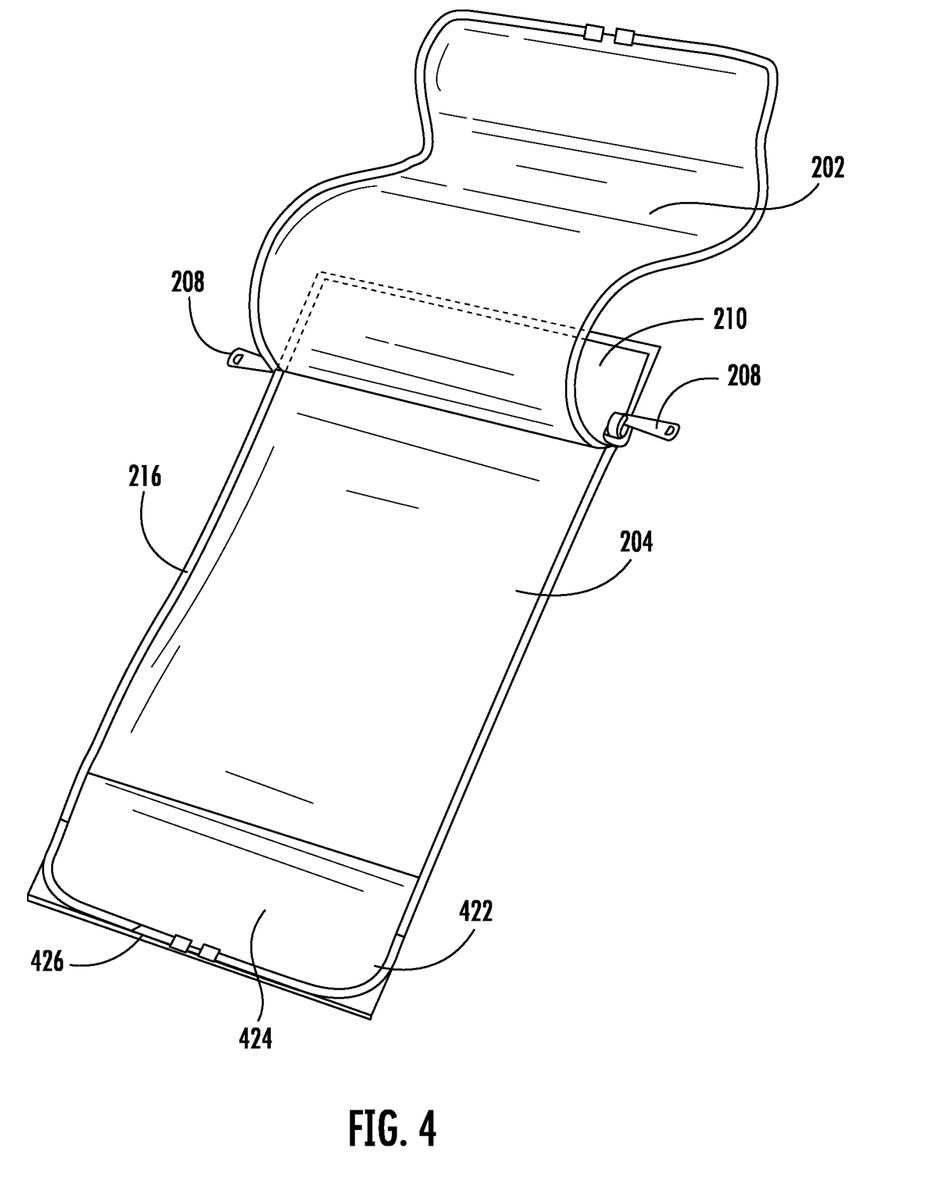
FIG. 4 illustrates a perspective view of a duvet cover in an open position of FIG. 2 according to some embodiments.

FIG. 4 illustrates a perspective view of a duvet cover 106 in an open position of FIG. 1 according to some embodiments herein. The duvet cover 106 with duvet 104 includes a third fabric panel 422 in the second end pocket 424. In some embodiments, the third fabric panel 422 is attached at the second end of the top fabric panel 202 and/or second end of the bottom fabric panel 204. In some embodiments, the third panel 422 is attached to the top fabric panel 202 and/or the bottom fabric panel 204 to create a composite panel. In some embodiments, the side edges and second end of the top fabric panel 202 is left unattached or free. In some embodiments, the third fabric panel 422 overlies the second end of the bottom fabric panel 204 to create a second end pocket 424 at the foot edge 426. In some embodiments, the foot edge of the duvet 104 is inserted into the second end pocket 424 in the foot edge 426. In some embodiments, the closable fastening device 208 is used to close and open the duvet cover 106. In some embodiments, two separate zipper chains are incorporated and the zipper chains begin at corresponding locations on either side of the duvet cover where joining of the top and bottom panels terminate. The zipper and/or zipper heads terminate and may meet at a midpoint of the lower end of the duvet cover. In some embodiments, with the duvet cover 106 in a fully closed position such that the duvet cover 106 is fully zipped, the two zippers and/or zipper heads meet at a midpoint of the lower end of the duvet cover 106.

Figure 5:
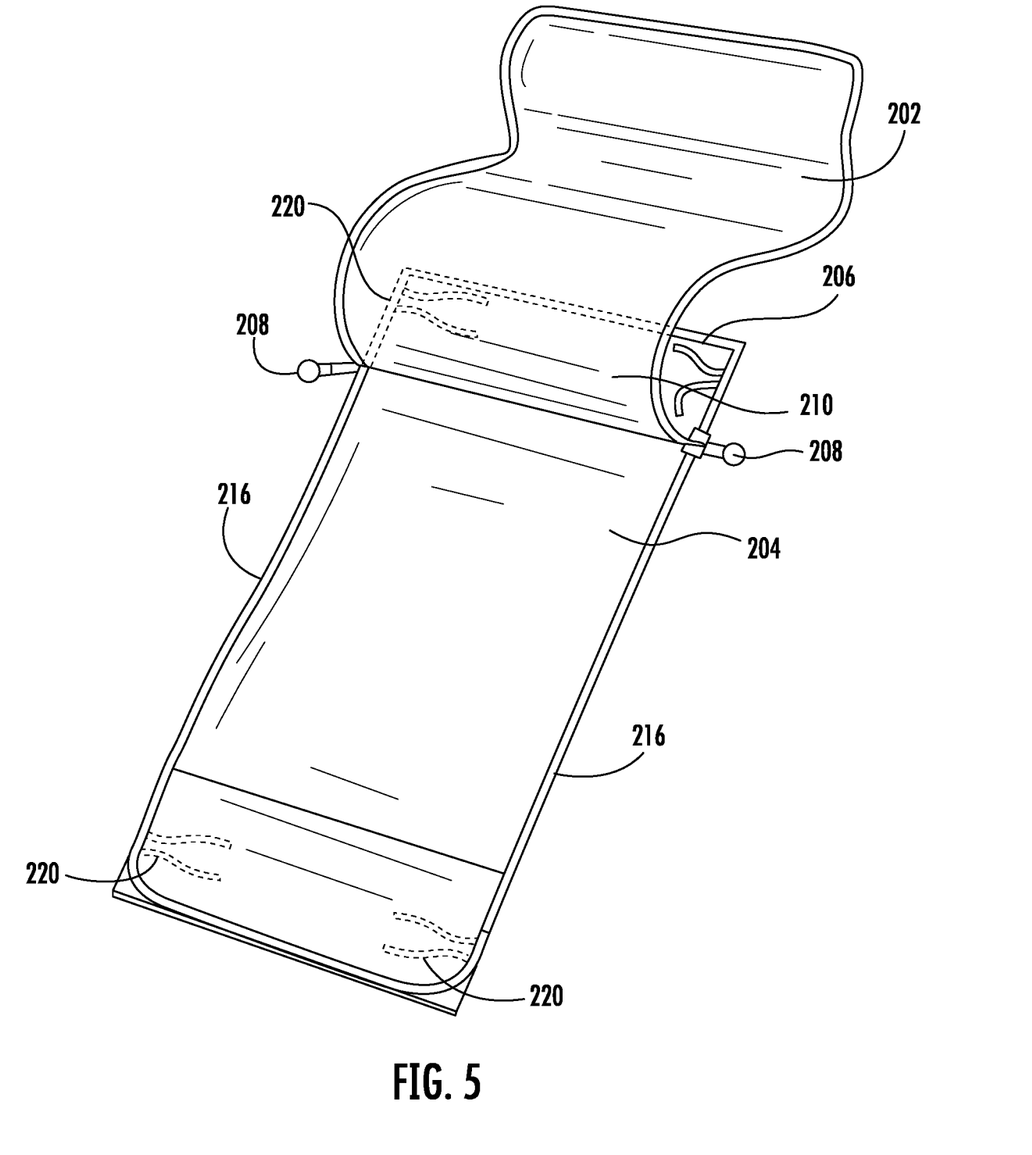
FIG. 5 illustrates a perspective view of a duvet cover with a pocket to secure the duvet of FIG. 2 according to some embodiments described herein.

FIG. 5 illustrates a perspective view of a duvet cover 106 with one or more pockets to secure the duvet of FIG. 1 according to some embodiments herein. The duvet cover 106 holds the duvet 104 inside. The head edge of the duvet 104 is inserted into the first end pocket in the head edge of the duvet cover 104. The foot edge of the duvet 104 is inserted into the second end pocket in the foot edge to secure duvet 104. In particular, the duvet 104 is secured in place so that it does not get caught in the zipper as the zipper is being used nor is zipper operation hindered. The closable fastening device 208 is placed on the side edges 216 and the bottom edges 426 of the top fabric panel 202 and the bottom fabric panel 204 to close and open the duvet cover 106 to protect duvet 104 while securing it in place. In some embodiments, the pair of first end pockets and second end pockets provides a professional envelope look. In some embodiments, the first end pocket and the second end pocket serve as snag guards, designed to shield the duvet from being caught in the one or more zipper chains when zipping or unzipping the duvet cover, thus facilitating the engagement of the fasteners while preserving their integrity and functionality, as well as the integrity of the duvet 104. In some embodiments, the duvet cover 106 gives an envelope look and feel to users and is more functional and user-friendly while presenting an appearance identical to that of a traditional cover. In some embodiments, with the duvet cover in a fully closed position, such that the duvet cover is fully zipped, the two zipper heads may freely meet at any point along the edges of the duvet cover. This embodiment offers flexibility with regard to the positioning of the zipper pulls in both the open and closed positions. In some embodiments, the duvet cover of the present invention allows for easy reaching to the corners of the duvet cover to accommodate a duvet without having to fold or roll the duvet cover 106, while securing the duvet in place within the duvet cover and/or ensuring easier insertion into and removal of the duvet from the duvet cover 106.

In some embodiments, a coded system is used to identify the attachment of the panels. For example, an underside of a bottom fabric panel in the duvet cover 106 can be coded to identify a different panel to be attached with the bottom fabric panel. The coded system may include the use of colors, letters, numbers, symbols, etc.

In still other embodiments, a coded system is used in the duvet cover 106 to identify matching corners for laying the duvet 104 in the duvet cover 106 correctly. Similarly to matching panels, the coded system for matching corners may include the use of colors, letters, numbers, symbols, etc.

In some embodiments, a color-coded corner system is used to identify matching corners for laying the duvet cover 106 correctly.

Embodiments of the present invention also provide a system that includes a housing and a duvet cover 106 as described herein. In some embodiments, the housing includes decorative packaging to appeal to purchasers of the system. The decorative packaging may include plastic and cardboard. The decorative packaging may also include a window on the packaging that allows the duvet cover 106 to be viewed therein. The decorative packaging may include a representative picture illustrating the duvet cover 106 in an environmental setting. Instructions describing how to use the duvet cover 106 may also be included in the packaging. The system may also include a duvet 104. Optional bedclothes may also be included in the housing. Optional bedclothes include, but are not limited to, sheets, pillowcases, pillow shams, bed skirts, and accent pillows and may form a bed-in-a-bag ensemble to complement the duvet cover 106 of the present inventive concept.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the spirit and scope of the appended claims.

What is claimed is:

1. A cover for housing an assembly, comprising:
a top fabric panel and a bottom fabric panel that together form a fabric envelope for receiving the assembly, wherein head edges of said top fabric panel and said bottom fabric panel are joined to form a closed head edge; side edges of said top fabric panel and said bottom fabric panel, adjacent to said closed head edge, are partially joined to form a first end pocket that spans a width of said top fabric panel and said bottom fabric panel; and remaining side edges of said top fabric panel and said bottom fabric panel and foot edges of said top fabric panel and said bottom fabric panel edges are equipped with a closable fastening device to engage each other thereby defining three edges that are closable and releasable; and
a composite fabric panel that forms a second end pocket attached to the bottom fabric panel and/or the top panel, wherein said composite fabric panel is created by joining a foot edge of a third fabric panel with a foot edge of the bottom fabric panel and/or the top panel;

and side edges of said third fabric panel with side edges, next to said foot edge of the bottom fabric panel and/or the top panel, wherein said closable fastening device comprises two separate zipper chains, wherein a first end of each zipper chain begins with either side edge of the cover and a second end of each zipper chain terminates with a midpoint of a foot edge of said cover, wherein the two separate zippers meet at the midpoint of the foot edge of said cover when zipping said cover, and wherein said first end pocket and said second end pocket serve as an insertion point for the assembly to be inserted into the head edge of the cover and the foot edge of the cover respectively, thereby securing the assembly in place inside the cover.

2. The cover of claim 1, wherein said cover comprises a binding accessory at at least two interior corners of the cover.

3. The cover of claim 1, wherein said assembly is at least one of a duvet, a comforter, a bed-in-a-bag, a blanket, a weighted blanket, a quilt, and a multi layered material.

4. The cover of claim 1, wherein said closable fastening device comprises a continuous zipper chain, wherein two separate zipper heads meet at any point along the three closable edges when zipping said cover.

5. A duvet cover for housing a duvet, comprising:
a top fabric panel and a bottom fabric panel that together form a fabric envelope for receiving the duvet, wherein a head edge of said top fabric panel and said bottom fabric panel are joined to form a closed head edge; side edges of said top fabric panel and said bottom fabric panel, next to said closed head edge, are partially joined to form a first end pocket which spans a width of said top fabric panel and said bottom fabric panel; and remaining side edges of said top fabric panel and said bottom fabric panel and foot edges of said top fabric panel and said bottom fabric panel edges are equipped with a closable fastening device to engage each other thereby defining three closable edges; and
a composite fabric panel that forms a second end pocket attached to the bottom fabric panel, wherein said composite fabric panel is created by joining a foot edge of a third fabric panel with a foot edge of the bottom fabric panel; and side edges of said third fabric panel with side edges of the bottom fabric panel, next to said foot edge of the bottom fabric panel,
wherein said closable fastening device comprises two separate zipper chains, wherein a first end of each zipper chain begins with either side edge of the duvet cover and a second end of each zipper chain terminates with a midpoint of a foot edge of said duvet cover, wherein the two separate zippers meet at the midpoint of the foot edge of said duvet cover when zipping said duvet cover, and wherein said first end pocket and said second end pocket serve as an insertion point for the duvet to be inserted into the head edge of the duvet cover and the foot edge of the duvet cover respectively, thereby securing the duvet in place inside the duvet cover.

6. The duvet cover of claim 5, wherein said duvet cover further comprises a binding accessory at four interior corners and optionally along the top edge of the duvet cover.

7. The duvet cover of claim 6, wherein said binding accessory comprises at least one of ties or clips.

8. The duvet cover of claim 5, wherein said closable fastening device is selected from at least one of zippers, buttons, clips, hooks and eyes, press studs, snaps, loops, ties or Velcro.

9. The duvet cover of claim 5, wherein at least two corners of said duvet cover comprise a shape of at least one of rectangular, square, hexagonal, rounded, rhombus or irregular.

10. The duvet cover of claim 5, wherein a coded system is used to identify matching corners for laying the duvet cover correctly and/or a color-coded or coded underside of the bottom fabric panel or topside of the top fabric panel in the duvet cover is used to identify the third panel attached with the bottom fabric panel or top fabric panel.

11. The duvet cover of claim 5, wherein the one or more fastening devices are attached to the four corners of the top fabric panel and bottom fabric panel to secure the duvet with optional fastening devices at the head edge and/or foot edge of the duvet cover.

12. The duvet cover of claim 5, wherein the closable fastening device is the same color as, similar to, or complementary to the color of the duvet cover.

13. The duvet cover of claim 5, wherein the closable fastening device is a different color and/or material from the duvet cover.

14. The duvet cover of claim 5, wherein the closable fastening device is a zipper that conforms to the shape of at least two corners.

15. A system comprising:
a housing; and
a duvet cover of claim 5.

16. The system of claim 15, wherein the housing includes decorative packaging to appeal to purchasers of the system.

17. The system of claim 16, wherein the decorative packaging comprises one of plastic and cardboard.

18. The system of claim 17, wherein the decorative packaging includes a window on the packaging that allows the duvet cover to be viewed therein.

19. The system of claim 15 further comprising a duvet.

20. The duvet cover of claim 5, wherein said closable fastening device comprises a continuous zipper chain, wherein two separate zipper heads meet at any point along the three closable edges when zipping said duvet cover.

* * * * *